United States Patent [19]

Anderson

[11] Patent Number: 5,073,495
[45] Date of Patent: Dec. 17, 1991

[54] APPARATUS FOR ISOLATING CLONED VECTORS AND CELLS HAVING A RECOVERY DEVICE

[75] Inventor: Norman G. Anderson, Rockville, Md.

[73] Assignee: Large Scale Biology Corporation, Rockville, Md.

[21] Appl. No.: 260,724

[22] Filed: Oct. 21, 1988

[51] Int. Cl.⁵ .................... C12M 3/00; C12M 1/26
[52] U.S. Cl. .................... 435/284; 435/292; 935/85
[58] Field of Search .............. 935/79, 80, 85, 87, 935/90, 111; 435/285, 284, 287, 291, 30, 294, 295, 293, 292; 118/691

[56] References Cited

U.S. PATENT DOCUMENTS

| | | |
|---|---|---|
| 3,694,317 | 9/1972 | Scher .................... 435/30 |
| 3,862,013 | 1/1975 | Pagano .................... 435/294 |
| 3,941,561 | 3/1976 | Noteboom . |
| 3,979,264 | 9/1976 | Buerger . |
| 4,476,226 | 10/1984 | Hansen et al. . |
| 4,504,547 | 3/1985 | Horodniceanu . |
| 4,565,788 | 1/1986 | Hansen et al. . |
| 4,657,873 | 4/1987 | Gadow et al. . |
| 4,659,672 | 4/1987 | Provonchee et al. . |

FOREIGN PATENT DOCUMENTS

| | | | |
|---|---|---|---|
| 3218857 | 5/1982 | Fed. Rep. of Germany | 435/292 |
| 3318287 | 12/1983 | Fed. Rep. of Germany | 435/30 |
| 87/07911 | 12/1987 | World Int. Prop. O. | 435/30 |

Primary Examiner—David L. Lacey
Assistant Examiner—William R. Y. Chan
Attorney, Agent, or Firm—Venable, Baetjer, Howard & Civiletti

[57] ABSTRACT

A method and apparatus are described for isolating samples of cloned vectors or cloned cells. A cell lawn is grown on a culture medium gel which is adhered to a film. Samples are grown on the cell lawn and then recovered therefrom by a series of hammers or thin sterilizable filaments, each of which lifts a sample from the cell lawn and transfers the sample to a site remote from the film.

33 Claims, 9 Drawing Sheets

APPARATUS FOR ISOLATING CLONED VECTORS AND CELLS HAVING A RECOVERY DEVICE

BACKGROUND OF THE INVENTION

The invention relates to molecular biology, and more specifically, to genetic engineering techniques for isolating samples of cloned vectors or cloned cells containing recombinant DNA. Cloned vectors are isolated from "shotgun" vector libraries, or vector libraries of any sort, and cloned cells include bacterial, yeast, fungal or eukaryotic cells.

When DNA is digested with restriction enzymes or sheared mechanically and the fragments cloned into suitable viral or phage vectors or inserted into cells by any means, a heterogeneous collection of vectors or cells results. These vectors or cells may then be individually isolated or cloned and grown to provide masses of particles which are identical, and which amplify the recombinant DNA present in the original individual isolated vector or phage or cell.

The amount of DNA in one vector is limited, averaging 4.1 kilobases for vectors in present use, such as Chiron II and similar vectors, and around 40 kilobases for cosmid vectors. Larger fragments may be grown in yeast, while masses of single human chromosomes may be produced in Chinese hamster cells, for example. Since the human genome contains approximately 3.4 billion base pairs of DNA, one million different lambda-scale phage clones or 100,000 cosmids would be required to span the entire human genome.

When amplification involves the use of virus or phage particles, cells must be provided in which these non-living particles can grow and multiply. Where the DNA is inserted directly into a cell under conditions in which it can multiply free from viral genome influence or control, then the requirement is to clone and select these cells directly. As mentioned, DNA may be directly inserted into yeast, for example, and human chromosomes can be arranged to multiply in cells of other species. In the latter case, cells containing one known chromosome are selected and cloned. Therefore, both cloning of infectious particles (vectors, viruses, phage, etc.) using living host cells and cloning of non-virus infected cells containing specific desired DNA inserts or chromosomes are required.

For a large-scale human DNA sequencing project, several different libraries of vectors containing DNA fragments produced by several different restriction enzymes will be required. The isolation, growth, processing, storage and analysis of large numbers of individual clones from large recombinant DNA vector libraries will therefore be an important activity as a first step in large-scale DNA sequencing, and completely automatic and robotic methods will be required for clone isolation.

To isolate vector clones using standard methods, the initial sample from the recombinant DNA vector library is diluted and applied to a lawn of E. coli or other organism in which the vector used will grow and produce cell lysis. Small clear areas are produced where lysis occurs. The vector, usually a phage, is recovered from these clear lytic spots, and grown en masse in additional cell cultures to yield the DNA required for sequencing. This is customarily done in petri dishes poured and infected by hand, the phage is diluted and applied manually (or added to the original bacterial cell suspension), and the phage "colonies" are observed visually and the phage recovered for further multiplication by a human operator. To improve efficiency, the vector may be genetically engineered to contain an enzyme which is active in those colonies which contain recombinant DNA inserts. This enzyme is chosen to yield an identifying color in the lytic spot when a suitable substrate is present. With this method, only colored spots are chosen. The enzyme product may also be fluorescent, in which case the choice is made on the basis of fluorescence. Detection may thus be by absence of light scatter in a clear zone, or by light absorption or fluorescence by an enzyme-produced dye.

If the amount of DNA is such that one million individual clones are produced in the initial library (termed a "heap" since it is not ordered or indexed), and if a million clones are isolated from this heap, then on the basis of pure statistical probability one would expect a little more than three-fourths of all clones to have been isolated. The remainder of the clones represent duplicates (and a few triplicates, etc.). Therefore, to approach isolation of all individual clones in the heap, repeated sets of a million clones would have to be isolated and intercompared. These considerations lead to the conclusion that many tens of millions of clones will require isolation as part of any attempt to sequence the entire human genome, and that clone isolation on this scale will require the application of automation and robotics.

The entire sequencing project becomes more efficient the larger the size of the initial fragments cloned, hence the interest in starting with either chromosome sorting, or with cells containing only one human chromosome. Such cells are ideally chosen for having small numbers of indigenous chromosomes, and for having chromosomes from which the human chromosome carried may be easily isolated. Cloning such foreign chromosome-containing cells may be done with the systems described here, but do not generally require large-scale cloning.

Fragments smaller than chromosome size may be inserted into yeast and the yeast grown to yield quantities of the insert. The fragments are generally produced by shearing or by the use of restriction enzymes which cut at rare sites (so-called "eight cutters," for example). Alternatively, digestion with restriction enzymes may not be carried to completion, yielding some long fragments which can be further cut by additional enzyme action. Cloning and selection of cells from such host yeast preparations will require cloning on a smaller scale than that required for various vectors, but even with yeast there is still a substantial amount of effort required to obtain a complete set of all possible clones.

SUMMARY OF THE INVENTION

The invention relates to an apparatus for isolating and separating samples of cloned vectors or cloned cells. The apparatus comprises a recovery means which selectively removes samples from a cell lawn carried by a film and transfers the removed samples to a site remote from the film. The cell lawn is grown on a culture medium gel which is attached to a film. The film includes spacers mounted thereon extending parallel to the lengthwise edges of the film, and the film is moved past the recovery means by drive rollers.

The culture medium gel is commonly adhered to the side of the film on which the spacers are mounted, and when stored in a rolled form, the spacers provide for sufficient air circulation between successive layers of the rolled film to support cell growth. Perforations can be provided along the lengthwise edges of the film to mesh with the drive rollers as the film moves past the recovery means. The perforations also allow for the reproducible determination of colony positions along the film.

The invention also relates to the method by which the apparatus is used to isolate and separate samples of cloned vectors or cloned cells. The method comprises applying a culture medium gel to an elongate film, growing a cell lawn on the gel, dispersing cloned vectors on the cell lawn, or alternatively dispersing individual cells containing DNA inserts on the gel, incubating the film (preferably in a rolled form), unrolling the film and recovering samples therefrom. The cloned vectors or cloned cells can be dispersed on the cell lawn from a jet nozzle orifice or by other means described, such as spraying, coating or dipping.

The invention also relates to the production of duplicate films by printing the original film pattern of colonies or spots onto a duplicate film. The films may be stored in dried or frozen form with or without cryoprotectants.

BRIEF DESCRIPTION OF THE DRAWINGS

The various objects, advantages and novel features of the invention will be more readily appreciated from the following detailed description when read in conjunction with the appended drawings, in which.

Throughout the drawings, like reference numerals are used to designate like parts and components throughout the various embodiments of the invention described in detail below.

DETAILED DESCRIPTION OF THE PREFERRED EMBODIMENTS OF THE INVENTION

The term "vector" is used to describe an infectious particle which contains recombinant DNA or RNA derived by methods known to genetic engineers and molecular biologists. The recombinant DNA or RNA is reproduced each time the nucleic acid of the infectious particle is reproduced. The vectors may be bacteriophage (phage), viral particles of any type, plasmids, cosmids or infectious nucleic acid.

The terms "host" and "host cells" are used to describe any living cell in which a vector, DNA fragment or chromosome may be reproduced, and may include bacterial cells, yeast, fungi or eukaryotic cells of any type.

The term "medium" is used to describe a mixture comprising water, salts and nutrients which will support the growth of host cells, and the replication of vectors in the host cells. A medium is also termed a culture medium and can be incorporated into a gel.

The term "gel" is used to describe a hydrophilic material which can be attached to a synthetic plastic film. The gel preferably has a high water content and can comprise a culture medium. The gel can therefore support the growth of host cells and the replication of vectors.

The term "sample" is used to describe cloned vectors or cloned cells.

The term "library" is used to describe an unsorted collection of vectors or host cells containing many different DNA fragments or inserts.

Figure 1:
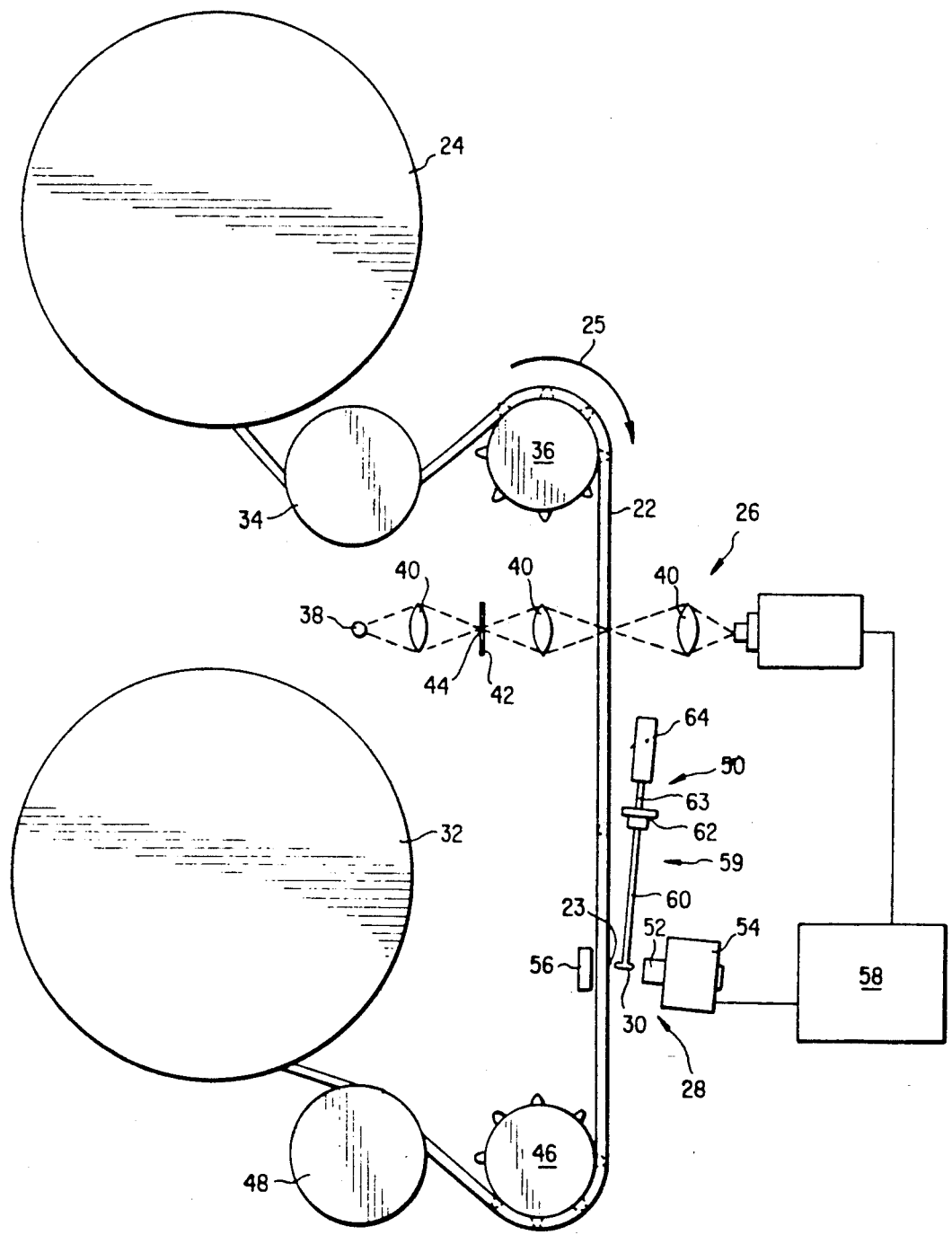
FIG. 1 is a schematic side view of the apparatus for isolating cloned vectors and cells constructed in accordance with the present invention.
Figure 2:
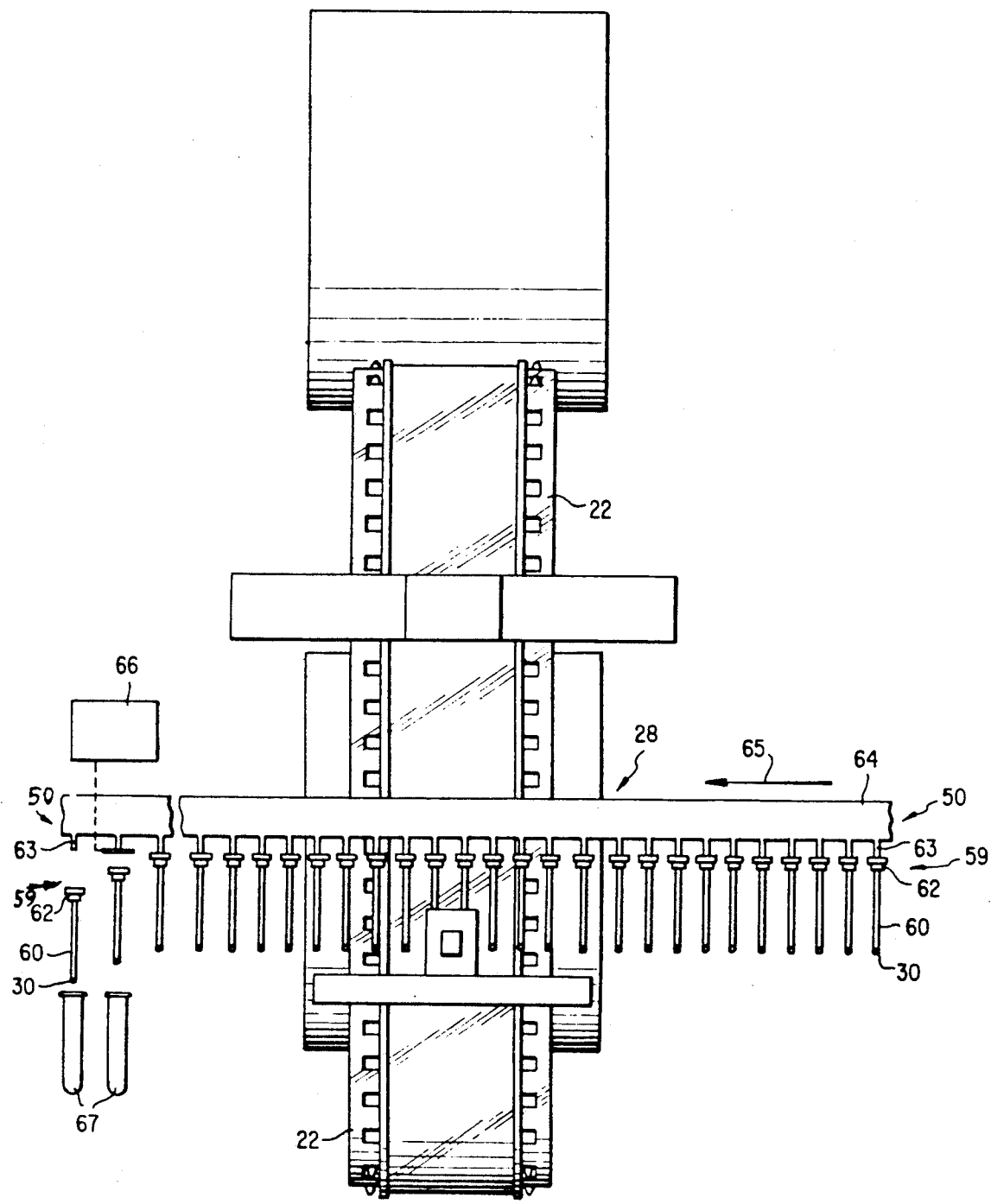
FIG. 2 is a partial frontal view of the apparatus shown in FIG. 1.

FIGS. 1 and 2 illustrate the apparatus and method used to isolate and recover samples. A film 22 with cloned vector samples or cloned cell samples thereon is unwound from a storage reel 24 in the direction of the arrow 25. The location of samples is detected by an optical scanner means 26, and the locational information is transmitted to a recovery means 28. The sample recovery means comprises a sample removal assembly, such as hammer assembly 50, having a plurality of pivotably mounted hammers 59. Each hammer 59 includes a tip 30 which is selectively movable in the manner described in greater detail below to engage a selected sample. Each sample is removed or "picked" from the film 22 by a hammer tip 30, and transferred to a site remote from the picking area. After picking of the sample, the film 22 is wound onto a second or "take-up" reel 32.

When the film 22 is unwound from the storage reel 24, it travels over an idler 34 and a sprocketed guide roller 36, and is inspected for the location of samples. The location of samples may be inspected visually at intervals by passing the film over dark field illumination under conditions which allow operator examination with or without magnification, and under conditions which minimize the chance for contamination. However, inspection is preferably performed automatically by passing the film 22 past the optical scanner means 26 which detects the location of each sample of interest on a cell lawn which has been grown on a gel medium attached to the film 22. The locational information for each sample of interest is transformed to a digitized format for use in coordinating the activity of the hammer assembly 50 with respect to the position of a sample of interest on the moving film 22.

The optical scanner means 26 includes a light source 38 and a train of lenses 40 which either employ a slit 42 at position 44 to allow a slit of light to be focused at the plane of film or alternatively an opaque bar (not shown), or other suitable means for imparting dark field illumination to the film 22. The scanner means 26 is conventional in nature and typically includes a linear photodiode array (not shown) for quantifying the amount of light which passes through the film. Filters (not shown) are typically included in the light train for absorbance or fluorescence measurements.

The scanner means 26 employs a standard charge-coupled device camera (CCD) and the scan frequency is set to scan at a rate of at least five lines through each lysis spot. While many image analysis techniques and programs are known to those skilled in the art, the simplest one involves locating the dye enzymatically produced by insert-containing phage, and is the preferred method.

Cells may be applied in a regular array using droplet producing-and vectoring technology such as is incorporated in conventional fluorescence cell sorters. When cells are applied by this method, a check will be made as part of the computational program to see whether any given spot is indeed within the area expected. The position of each spot is computed from the fluorescence or absorption maxima.

Preferably, the samples are vectors comprising phage which create lytic spots on the cell lawn. The scanner means 26 in combination with computer 58 digitizes the film image as the film 22 is continuously moved past the scanner means in the direction of arrow 25 by a film transport system generally comprising a drive roller 46 and an idler 48. The digitized image, in a manner well known in the art, comprises a plurality of lines of picture elements ("pixels") giving a uniformly high signal due to the scatter of light from the host cell lawn.

Lytic spots are indicated along a single scan line by a sudden drop in signal which continues on to the end of the lytic spot. If dye containing spots are created by the samples, such spots are indicated by increased absorbance. Spots containing fluorescent dyes are detected by light emission from the spots.

By averaging a line of pixels around a given pixel for a long distance in both the horizontal and vertical directions, a "background" value is obtained which is compared with the value of the pixel under consideration at a given instant. Differences (plus or minus, depending on the detection methodology employed) greater than a preset value are considered as a positive, and all positive values are saved. When a set of positive values is accumulated, and when no adjacent value is positive, the set of pixels defining a spot is considered complete. The location of the center pixel is then determined, and the coordinates used to energize the recovery means 28 which recovers the sample. The development of computer image analysis programs to find the centers of spots is well known to those skilled in the art.

The digitized information from the scanner means 26 is transmitted to a microprocessor 58 which in turn, after a computed delay interval, transmits digitized information to the sample recovery means 28. The location of each sample of interest is communicated digitally to the hammer assembly 50 of the recovery means 28. The hammer assembly 50 preferably comprises a support member in the form of a belt 64 having a plurality of individual hammers 59 that is movable laterally across the face of the film 22 in a direction generally transverse to the direction of film travel. The hammer assembly 50 includes a movable plunger 52 selectively actuable by a solenoid 54. When a hammer tip 30 is positioned over a selected sample, such as sample 23, the plunger 52 is actuated and directed into engagement with the hammer tip 30, causing the tip 30 to strike the sample 23. The sample 23 is supported in the vicinity of the hammer assembly 50 from below by a platform 56. An unused hammer tip 30 is moved in place for each sample to be recovered. The digitized information from the microprocessor 58 is used to position the hammer tip 30 over the desired sample 23 and to activate the solenoid 54 to cause the plunger 52 to strike the hammer tip 30 at the moment the desired sample is directly beneath the tip 30.

In a preferred embodiment, the hammer tip 30 is attached to one end of a hammer shaft 60. The other end of the hammer shaft 60 is connected to an enlarged member in the form of an end cap 62 which serves as a cap for a vessel 67 (FIG. 2) used for sample storage. The enlarged end cap 62 couples the hammer 59 to the hammer support member or belt 64 through a rod 63. The hammer 59 is severable from the belt 64 at the end cap 62 in the manner set forth below to provide an uncontaminated sample stored within a storage vessel 67.

Following contact with the desired sample 23, the hammer tip 30 rebounds from the film 22 and the hammer assembly 50 is moved in the direction of the arrow 65 transverse to film 22, as shown in FIG. 2. A fresh, unused hammer tip 30 is then positioned over the film 22 and beneath the plunger 52. The process described above is repeated to recover further samples from the film 22.

The hammer tip 30 is preferably in the form of an inverted cone analogous to the letter "O" on a typewriter's daisy wheel. However, any construction configured to retain a sample of gel, such as a tip having gel-retaining grooves or serrations, is suitable for the tip.

As shown in FIG. 2, at a site remote from the film 22, individual sample-containing hammers 59 are cut at the point of connection of the rod 63 to the end cap 62 by a cutting means 66. Following cutting, the hammers 59 are directed into a sample-receiving vessel 67, such as a test tube, the open end of which is securely sealed by the end cap 62 following entry of the hammers 59. In a preferred aspect of the invention, the sample vessels 67 and hammers 59 are indexed relative to one another such that an available sample vessel 67 is positioned beneath a corresponding hammer 59 at the moment the hammer is severed from the hammer support member or belt 64. As a consequence of the transverse, vertical orientation of the hammer support belt 64 relative to the film 22, the severed hammers 59 fall from the belt into the awaiting sample vessels. Parameters such as the height of the fall, hammer and vessel material composition and thickness, and end cap 62 dimensions are selected so as to optimize the collection of samples 23 from the film 22 while at the same time minimizing losses resulting from hammer and/or sample vessel breakage, scraping of the hammer tips against vessel sidewalls, and the like. Known conveyance or carriage apparatus can be utilized in conjunction with the aforedescribed embodiment to provide for sample vessel conveyance both toward the cutting means and away therefrom following receipt of a sample-containing hammer. While the sample vessel 67 and corresponding hammer 59 are preferably stationary at the time of hammer severance from the belt, persons of ordinary skill in the conveyance art will appreciate that such need not be the case and that the paths of sample vessel 67 travel, hammer support belt 64 travel and hammer 59 fall following severance can be readily coordinated to insure secure arrival of a single, sample-containing hammer 59 into a corresponding sample vessel 67. Sample vessels 67 may be empty or may contain growth medium, and may be attached together so that the recovered samples are more easily stored, numbered, identified and recovered.

The hammer assembly 50 may also be cut into sections which fit into rows of attached sample vessels 67 for cultivation. Thus, for example, one hundred hammers 59 could be cut off as one unit, and all of the hammers simultaneously inserted into a row of one hundred attached vessels 67. The sample vessels 67 would be simultaneously sealed by the caps 62. Such an attached set of vessels would simplify storage and subsequent identification.

Figure 3:
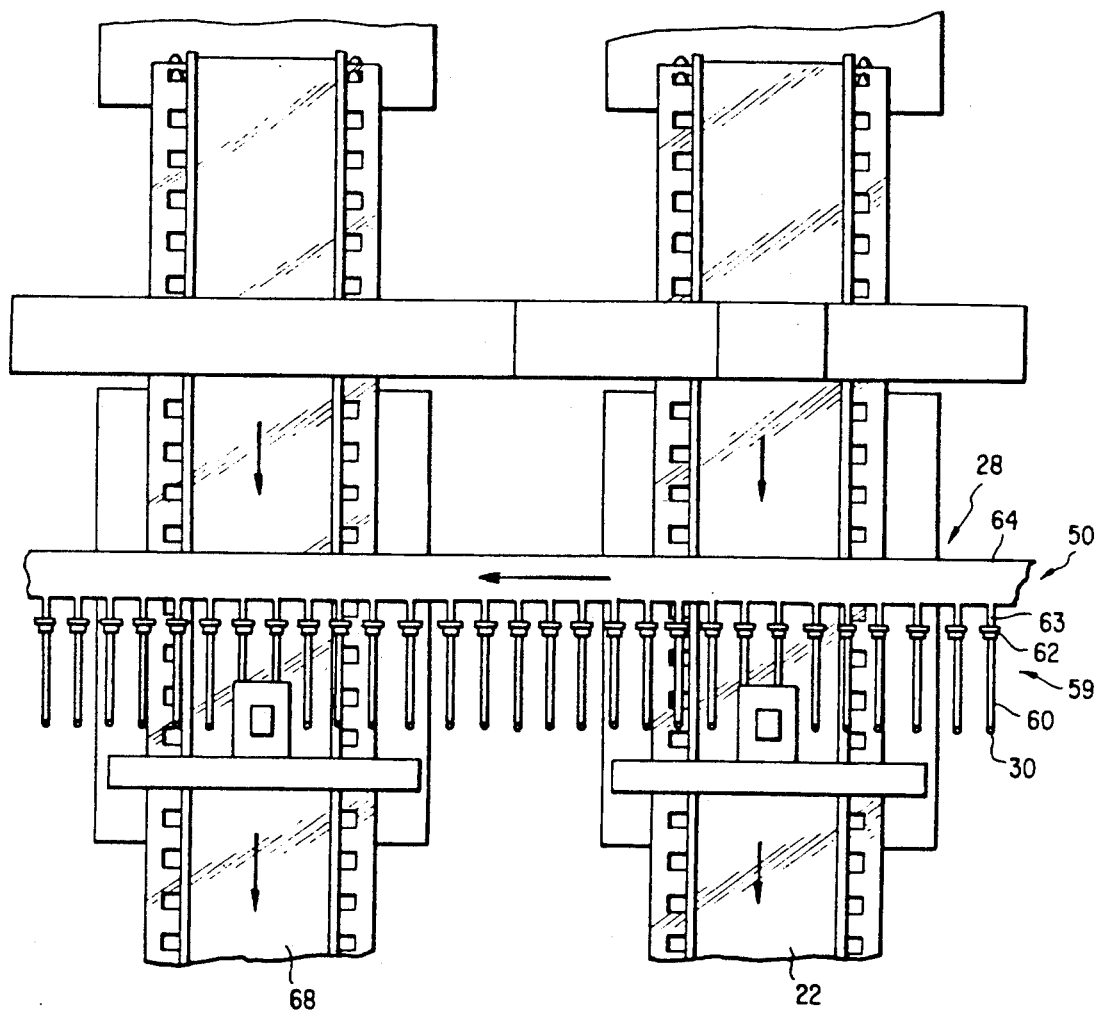
FIG. 3 is a frontal view of an alternative embodiment recovery means of the apparatus depicted in FIGS. 1 and 2.

Alternatively, rather than inserting the hammers 59 into the sample vessels 67, each hammer tip 30 can be used to transfer all or part of a sample by touching the sample onto another gel medium, as shown in FIG. 3. The gel medium may be on a second film 68 which could be marked to identify isolated DNA samples. This second film 68 may be of a different composition and may be of porous nitrocellulose or nylon which absorbs DNA and can then be passed through a solution of a single known labelled DNA in order to identify specific complementary DNA on the film.

Figure 4:
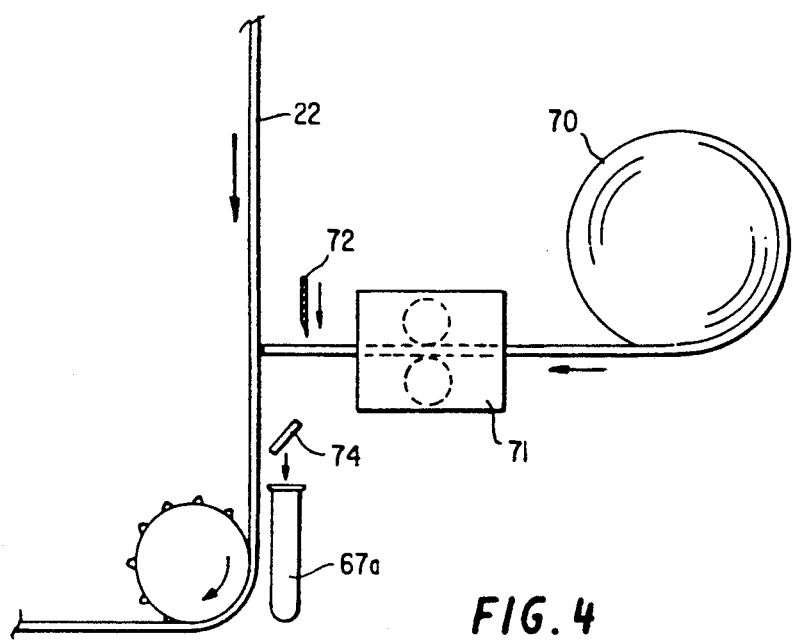
FIGS. 4 and 5 are schematic side views of alternative recovery means of the apparatus shown in FIGS. 1 and 2.

Further, alternate methods for recovery of samples include the use of a supply of a reel 70 of suitable sample-retaining medium, such as narrow bore plastic tubing which is advanced through an indexing and advancing device such as a solenoid 71, as shown in FIG. 4. After the tubing 70 has been pressed against a sample, the tube is retracted and cut off by cutting device 72. The cut-off section 74 is either dropped into a sample vessel 67a directly, or may be grasped by a moving member and moved to a storage container. The supply of tubing is then advanced to give a freshly cut sterile surface to be used to recover the next desired sample.

Figure 5:
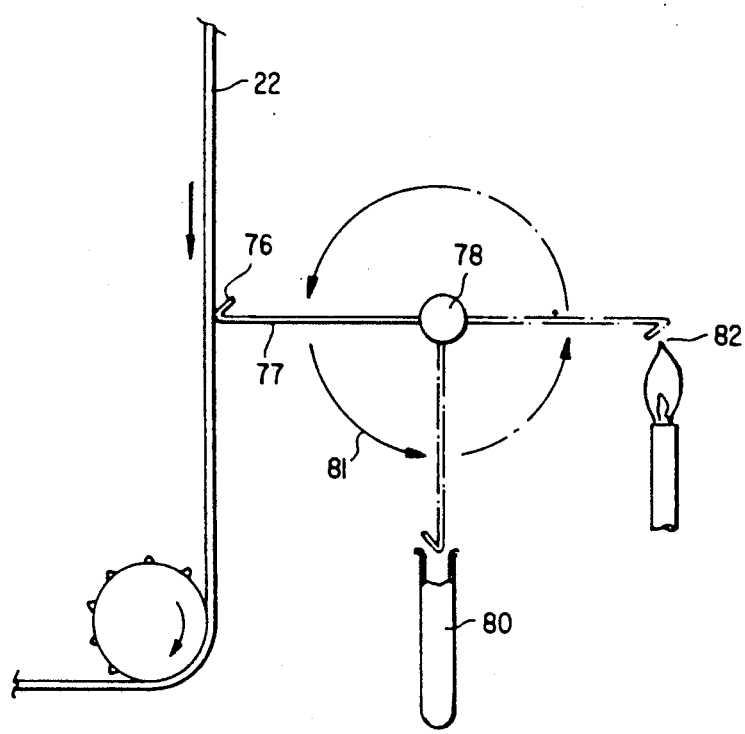

An additional method for recovering samples shown in FIG. 5 involves the use of a "V"-shaped filament 76 of platinum or other heat-sterilizable metal attached to a movable arm 77 which positions the "V" precisely over a sample. The "V"-shaped filament 76 is moved by a solenoid 78 into brief contact with the sample. The arm 77 is then withdrawn and moved into position to allow the filament 76 to transfer the sample into a waiting vessel 80 containing a culture medium or cells that is moved relative to the arm 77 in the direction of the arrow 81. The filament 76 is then briefly heated at position 82 to burn off remaining sample and to sterilize the filament for subsequent use. The filament may be sterilized by externally applied heat, or by passing a current through the filament itself. The sampling process may then be repeated for further samples.

Any of the samples collected may be dried and preserved for storage until needed at a later time. Such storage is possible whether the samples are present in sample vessels or on gel-covered film.

The above-described apparatus is useful in performing a process for isolating samples comprising cloned vectors or cloned cells. The process is described in terms of collecting isolated vectors, but applies equally to collecting isolated cells.

Figure 7:
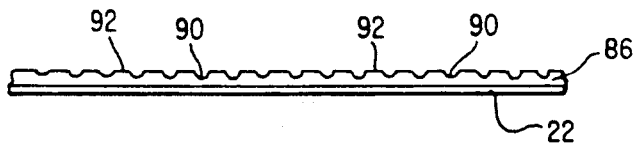
FIG. 7 is a side view of the film shown in FIG. 6.
Figure 8:
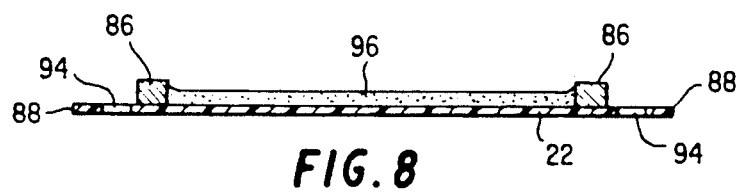
FIG. 8 is an end section view of the film shown in FIG. 6.
Figure 6:
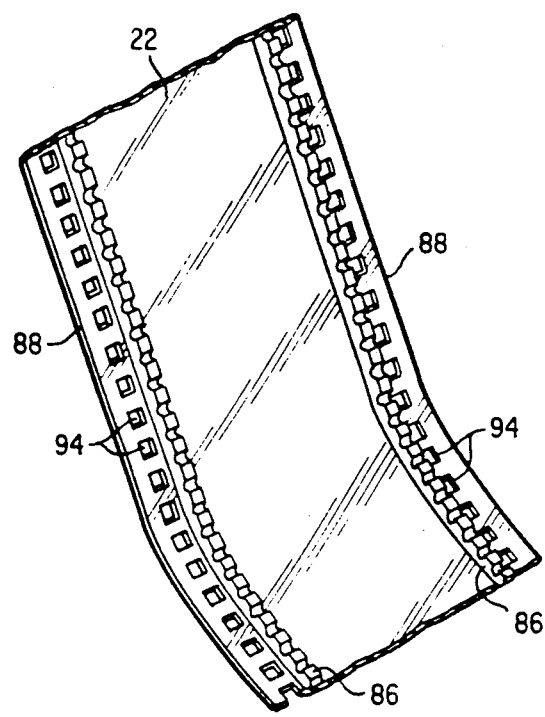
FIG. 6 is a top perspective view of the film used with the apparatus shown in FIG. 1.

With reference to FIGS. 6-8, there is depicted a strip of film 22 for use in conjunction with the present invention initially resembling or identical to film of the type used in motion pictures, and the like, having a plurality of sprocket apertures 94 along its longitudinal edges 88 for engagement by the sprocket wheel of a suitable film advancing device, but which is modified in accordance with the invention by the attachment of flexible spacers 86 adjacent the longitudinal edges 88 of the film. The flexible spacers 86 are configured in such a manner that the film surfaces are kept apart when rolled on a suitable reel. The spacers 86 are preferably mounted on the film 22 parallel to each other as well as the longitudinal edges 88 of the film and the array of sprocket apertures 94.

As best shown in FIG. 7, the spacers 86 are notched, thereby providing valleys 90 and ridges 92 along the extent of the spacer 86. When the film 22 is wound upon itself into a rolled form, the valleys 90 and the ridges 92 provide openings through which air can circulate. Effective air circulation for the film in a rolled form can be accomplished in a number of other ways, including the provision of perforated, serrated or porous spacers.

Figure 9:
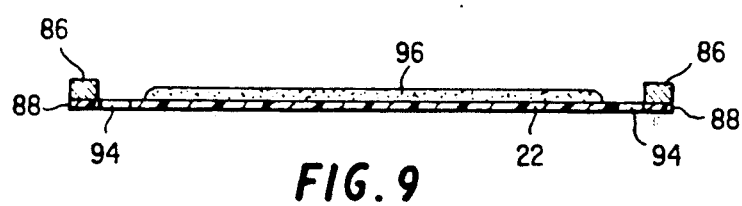

In an alternative embodiment shown in FIG. 9, the sprocket apertures 94 may be located at positions inside or between the spacers 86. The apertures 94 ease the movement of the film 22 over the sprocketed drive rollers 46 and guide rollers 36 (FIG. 1) by providing for positive indexable film transport when the film is used in the inventive process.

With reference once again to FIG. 8, the film 22 is shown with a gel 96 adhered thereto. In the embodiment of FIG. 8, the gel 96 is confined between the spacers 86. However, in alternative embodiments shown in FIGS. 10 and 11, the gel 96 may also be adhered to the side (face) of the film not having the spacers.

Figure 10:
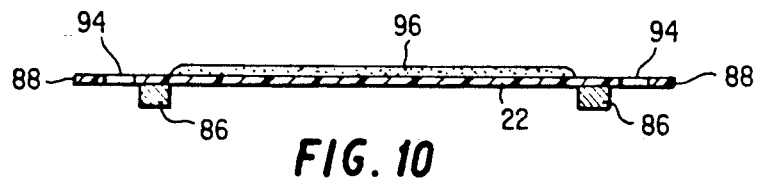
FIGS. 9-12 are end sectional views of modified embodiments of the film used in the apparatus depicted in FIGS. 1 and 2.
Figure 11:
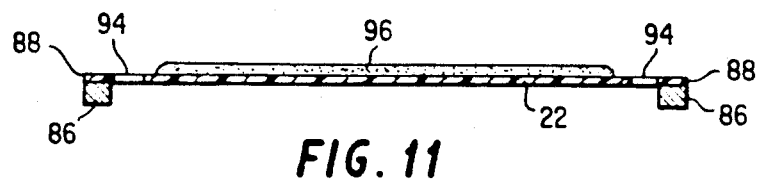

By changing the positions of the spacers 86 and the sprocket apertures 94 relative to one another, and varying the side of the film 22 to which the gel 96 is adhered, a variety of alternative embodiments of film 22 are possible. These alternative embodiments include those shown in FIGS. 9-16. FIG. 9 shows the gel 96 adhered to the film 22 on the same side as the spacers 86, but the sprocket apertures 94 are located inside or between the spacers 86. FIG. 10 shows the gel 96 adhered to the opposite side of the film 22 from the spacers 86, with the sprocket apertures 94 located between the spacers 86 and the longitudinal edges 88. FIG. 11 also shows the apertures 94 between the spacers 86, but with the gel 96 adhered to the film 22 on the opposite side with respect to the spacers 86.

Figure 12:
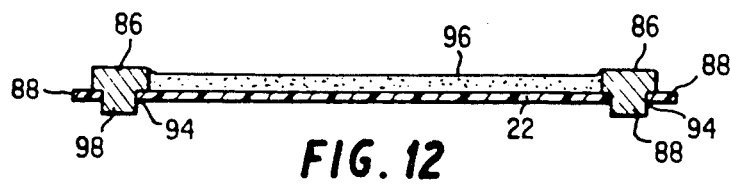
Figure 13:
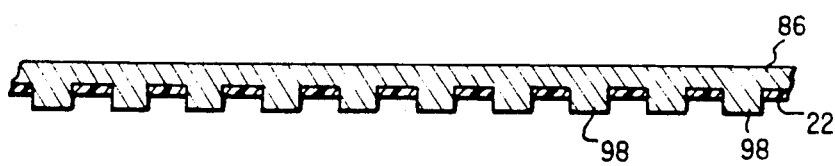
FIG. 13 is a side sectional view of the film shown in FIG. 12.

As shown in FIGS. 12 and 13, the spacers 86 may also be fabricated with teeth 98 which fit tightly into the film apertures 94. The teeth 98 project through the film apertures 94 to provide a second set of notched spacers on the opposite side of the film 22. Sprocket apertures normally used in motion picture film may be employed as indicated, however, additional apertures made specifically for the spacer teeth 98 may also be included in the film, thus providing both a set of sprocket holes for transport and a second set for spacer attachment.

Figure 14:
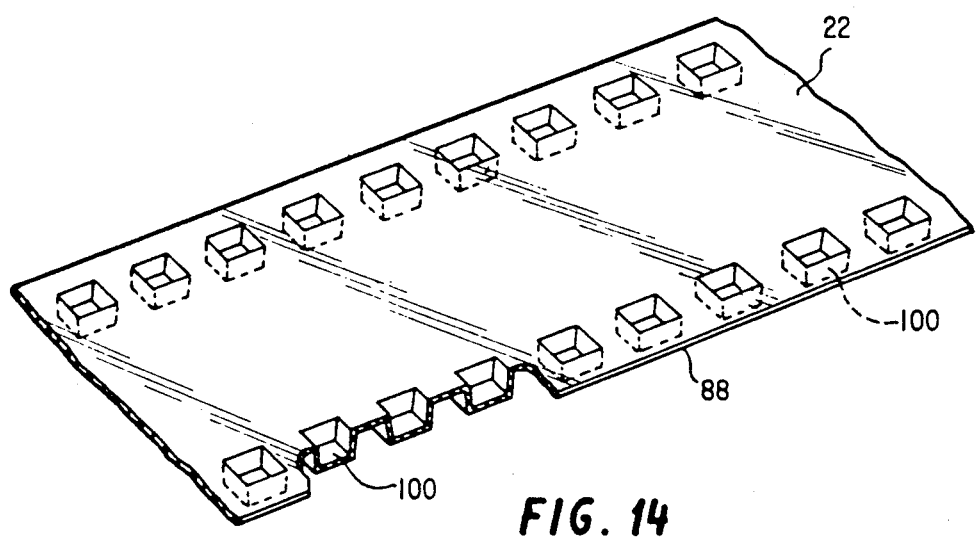
FIG. 14 is a perspective view of the underside of a modified embodiment of the film with part of the film shown in section, in which the spacers are embossed in the film itself.

As shown in FIG. 14, spacers 86 may also be formed by embossing, stamping or thermoforming the film 22 to make indentations. The indentations form tooth-like projections 100 which separate contiguous film layers when the film 22 is wound on a reel. In a film such as that shown in FIG. 14, the gel is confined to the center area of the film during casting by stationary walls attached to the casting apparatus (not shown). The gel may be attached to either side of film 22 in FIG. 14.

Figure 15:
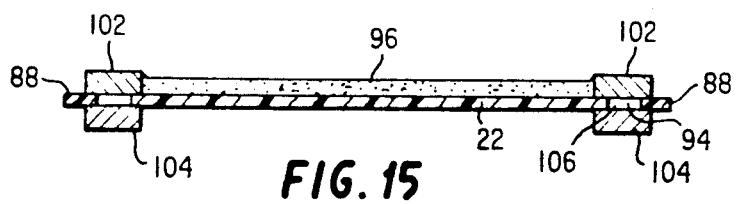
FIG. 15 is an end sectional view of a further modified embodiment of the film.
Figure 16:
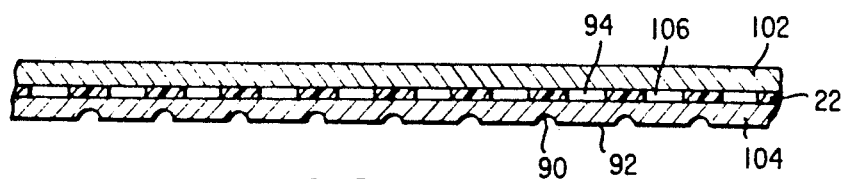
FIG. 16 is a side sectional view of the film shown in FIG. 15.

The film 22 is usually 5-10 mils thick, making it feasible to use two sets of spacers 102 and 104 as shown in the embodiments of FIGS. 15 and 16. An upper spacer 102 and a lower spacer 104 are held together by a flexible cement 106 which projects through the film apertures 94 or through a separate set of holes made for this purpose. One or both of the spacers 102, 104 may be serrated to create valleys 90 and ridges 92 as discussed above and illustrated in FIG. 7.

Figure 17:
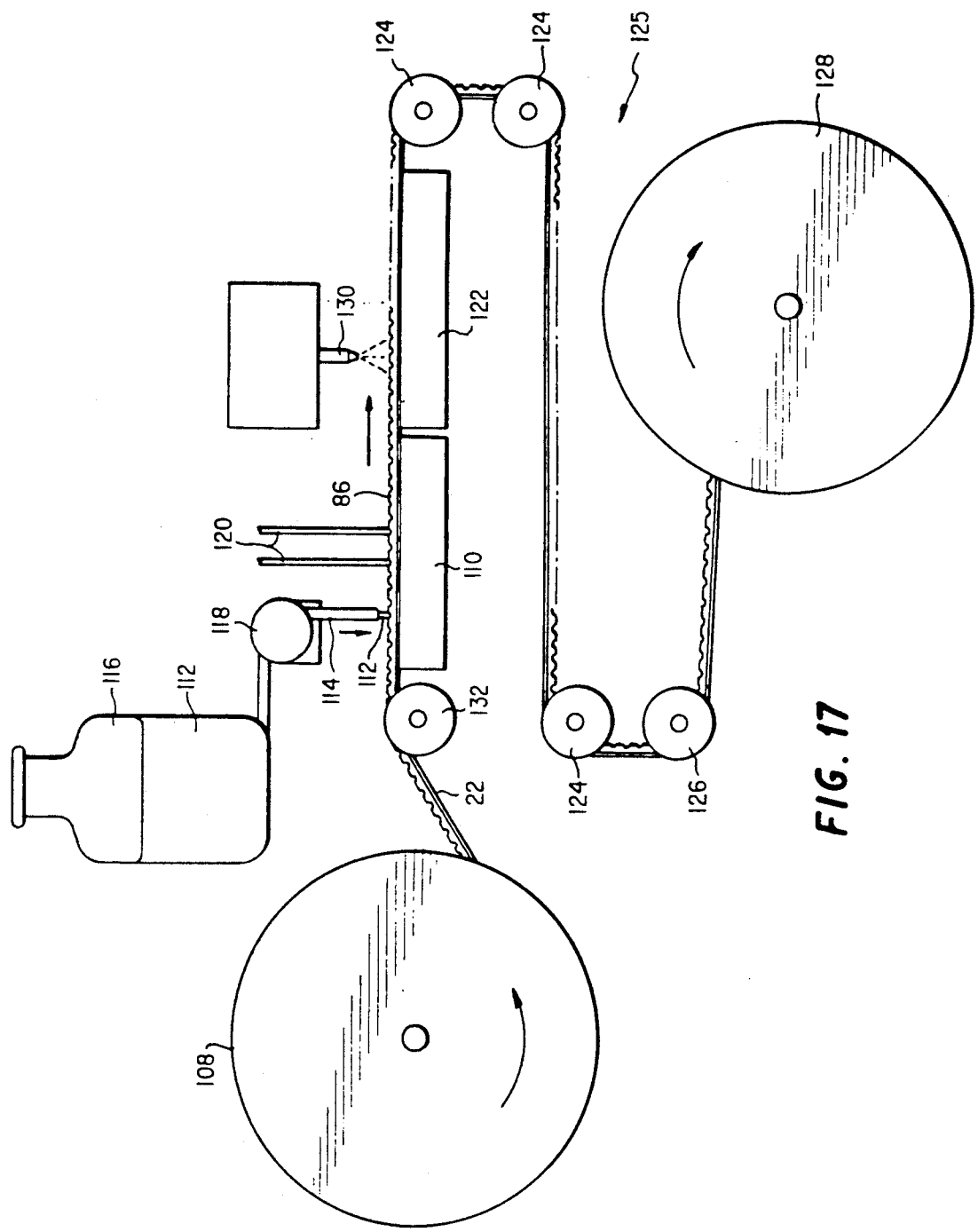
FIG. 17 is a schematic side view of the apparatus used to produce the film shown in FIG. 6.

FIG. 17 illustrates the apparatus and method by which the gel is deposited onto the film 22. The film 22 is unwound from a reel 108 and is passed a over heater 110 as culture medium 112 is applied through a nozzle 114 from a container 116 by a pump 118. The container 116, in which medium 112 is stored, is preferably heated.

At least one spreader 120 produces an even coating of medium 112 between the spacers 86 while the medium 112 is in a liquid or semi-liquid state and positioned over heated vacuum plate 110. After the spreaders 120 have leveled the medium 112, the film 22 is passed over a cooling unit 122 which chills and solidifies the culture medium 112 into a gel 96. The film 22 then moves over a series of guide rollers 124 in a chilled environment 125 under the power of a drive roller 126 and is wound onto a storage reel 128.

The culture medium 112 applied to film 22 may be applied with cells and vectors included so long as the ratio of cells and vectors is carefully controlled. Alternatively, the medium 112 may be applied with cells, but without vectors. When the medium 112 with cells is applied, then storage reel 128 is incubated to permit a cell lawn to grow on the gel 96. If necessary, the reel 128 can then be kept at a reduced temperature to minimize metabolic activity until used.

When only culture medium 112 is applied to film 22, the cells and vectors are preferably applied to gel 96 in separate steps by a jet nozzle 130 (FIG. 17) using the general principles of ink jet printing. The cells can also be applied to gel 96 by other methods including spraying, coating or dipping.

FIG. 17 also illustrates the application of vectors to the cell lawn on the film 22. As the film 22 is unwound from the storage reel 108, it passes over the idler 132 and past the jet nozzle 130 which applies a controlled distribution of vectors onto the cell lawn. The film 22 is then wound on the second reel 128 and incubated to promote vector replication.

Figure 18:
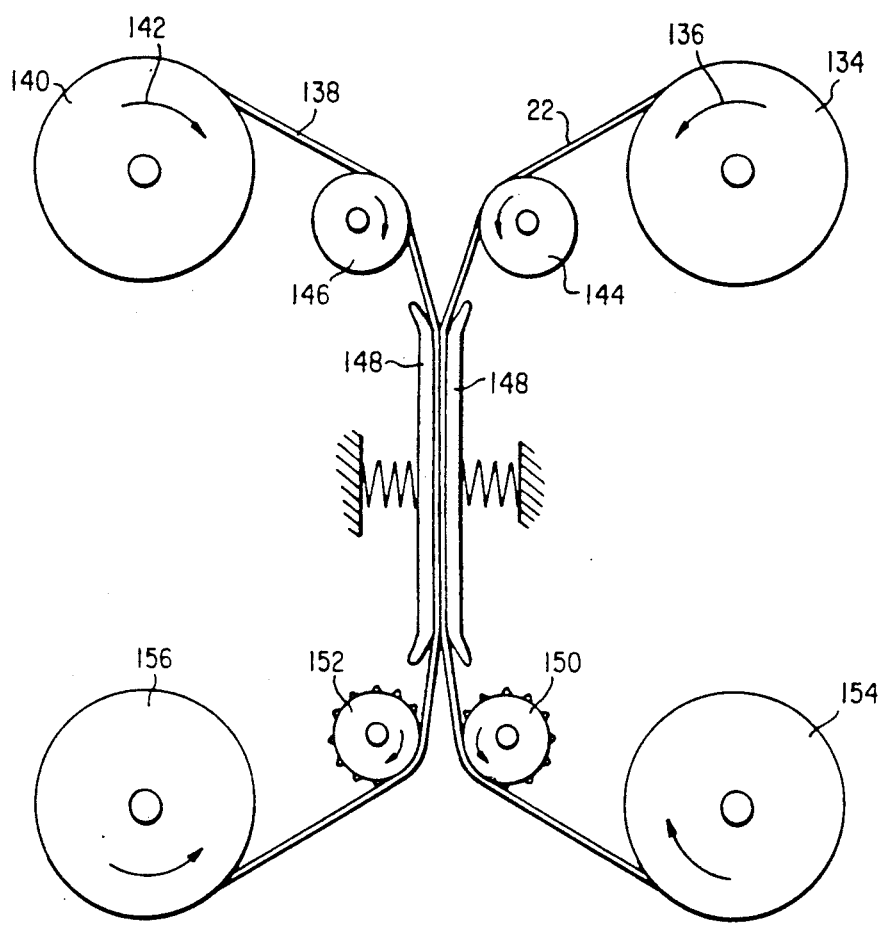
FIG. 18 is a schematic side view of an apparatus for transferring samples from one film to a second film.

An advantage of having the gel cast on the opposite side of the film from the spacers, as illustrated in FIGS. 10 and 11, is that colonies on an original film may be printed onto a second similarly constructed receiving film to produce a duplicate which is reversed left to right. This is done by lightly pressing the two moist films together, as shown in FIG. 18. The original film 22 with samples growing thereon is moved from reel 134 in the direction of arrow 136 as the receiving film 138 is moved from reel 140 in the direction of arrow 142. The original film 22 and the receiving film 138 are brought into close proximity after passing over respective guide rollers 144 and 146. The two films are then passed between pressure plates 148 where the original film 22 and the receiving film 138 are brought into contact with each other due to force exerted by the pressure plates 148. This force may be constant or intermittent.

After clearing the pressure plates 148, the original film 22 and the receiving film 138 separate from one another and pass over their respective drive rollers 150 and 152. Each film is then wound onto a respective second storage reel 154 and 156.

When the original film 22 contacts the receiving film 138, samples from the original film 22 are printed onto the receiving film 138 in a reversed left-to-right order. This process is similar to that used in the original technique for producing technicolor motion picture color release prints, and was called imbibtion printing, and involved transfer of dye from one film to another.

Thus, the system here described allows very large numbers of colonies or lytic spots to be produced, allows duplicate films containing the same spots to be produced, allows the cells from each colony or spot to be recovered individually and grown in suitable medium-containing vessels, and allows each colony to be identified by position on the film and by culture tube number.

The original or duplicate film with adhering colonies may be dried and/or frozen at low temperature for long-term storage, with or without the use of cryoprotectants which may be either incorporated into the gel as cast, or subsequently sprayed on.

Note that the original and duplicate films may have attached gels of different composition, that the film itself may be different from that of the original and may be porous, and that a porous duplicate film may be employed without attached gel to produce a duplicate.

The following portion of the specification discusses the properties and composition of the film 22 and the gel medium 96, as shown in the drawing figures. Reference numbers are used in this section of the specification only to identify previously described physical and mechanical features of the film 22 and the gel 96.

The film 22 from which the samples are recovered is treated on at least one side so that a hydrophilic gel medium 96 can be firmly attached. Along a longitudinal edge of the film 22, the film may have sample-identifying markings such as edge numbering or bar coding.

The film 22 may be formed of a cellulose derivative such as cellulose acetate, or may be a polyester or other synthetic material which has the necessary attributes of strength, transparency and ready availability. Preferred film materials include Mylar ® and Estar ®.

The film 22 may also have one of a variety of widths, the upper limit of which being determined by the curvature of the film when wound on a reel, the thickness of the film and the thickness and resilience of the spacers 86. The film width must be such as to impart the necessary strength to keep the film surfaces held apart by the flexible spacers 86 when wound on a reel. For use in the invention, 75 mm film or 105 mm film is preferred.

A variety of different types of gels 96 may be used to support the growth of host cells and the multiplication of vectors in them. These include, among others, gelatin, acrylamide, agar and its derivatives, polyethylene oxide gels, and any synthetic cross-linked polymer which can be made to adhere to the film support, contain the medium, and be non-toxic to the host cells and to vector replication. Adherence of the gel 96 to the film 22 may be facilitated by chemical modification of the film 22 to produce adhering groups. Alternatively, a layer of a gel 96 which will adhere securely, such as modified gelatin, may be used, and secondarily overlayered with a film of other gel-forming material which will adhere to the initial gelatin layer. The single- or multiple-component second gel may attach covalently to the initial gel, may interpenetrate it, or may be attached by secondary forces, and may be composed, for example, of gelatin, agarose, acrylamide, or other gelling material. Gelation may also be induced by radiation, and the film base may be chosen or modified to allow the gel to become attached to it covalently during radiation.

The gel material used may also be rehydratable. Rehydratable gels may be dried, stored for prolonged periods in dry form, and rehydrated either with medium or with controlled volumes of water. In the latter case, sufficient nutrients would be retained within the dried gel to support host cell growth and vector reproduction. If the gel is produced and dried without nutrients, these may be included in the rehydrating solution. Air squeegees, well known in motion picture film processing, are used to remove excess fluid after rehydration.

The fully hydrated gels may have any convenient thickness, but a thickness of approximately 0.25 mm to about 3.0 mm is useful for most applications, with a thickness of about 0.5 to about 1.0 mm being preferred. Film preparation and gel attachment and storage, with or without drying, must be done under sterile conditions. Sterility may be insured by sterilization of the film with attached gel by exposure to ultraviolet or ionizing radiation, or to ethylene oxide. Diethyl pyrocarbonate may also be added to the gelling medium 112 to sterilize it. This compound then decomposes to $CO_2$ and water, yielding a sterile non-toxic gel.

Four methods are commonly employed to distribute samples on gel-coated film 22. The samples comprise either vectors distributed among the cells in which they multiply, or individual cells containing inserts distributed evenly on the gel-coated transport film 22.

In a first method, bacterial cells and vectors such as phage are mixed with the gelling medium which is applied to the film 22 and allowed to gel. The concentration of the vectors is adjusted so that there is a very high probability that each lytic spot which develops contains the progeny of only one vector particle. Similar dilution procedures are used with yeast or other cells containing inserts so that each cell yields a separate colony.

In a second method, the cells and vectors (or insert-containing cells) are put on the surface of the gel after it has set. This may be done by applying the suspensions by dipping, by application with rollers or spreading bars, or by spraying to produce small droplets which settle on the surface.

In a third method, vectors and cells or insert-containing cells are applied to the precast gel using a device similar to an ink jet printer to place a series of evenly spaced droplets of identical size in a uniform pattern on the film surface. These first three methods depend on dilution and statistical probability to insure that each individual lysis spot or colony is the product of one original infectious unit or cell, and hence contains only one species of inserted DNA.

In a fourth method, which is applicable only to insert-containing cells, an advanced version of a cell sorter is used to detect individual cells in a flowing stream. The stream is segmented into droplets, and the droplets are electrostatically deflected. Only droplets containing single cells are deflected onto the gel surface to produce an even and highly regular pattern. The cells are detected and the cell-containing droplets are electrostatically deflected using systems and methods well known to those engaged in the art of cell sorting.

With regard to the third method discussed, there are two well known ink jet processes by which the cells and vectors may be applied in the present invention. In a continuous ink jet process, the suspension of cells or vectors is electrically charged, and when dispersed from the jet nozzle, droplets of the suspension pass between charged plates which direct the droplets to a specific area on the gel or cell lawn by exerting an attractive or repulsive force on each droplet. In contrast, a drop-on-demand ink jet process dispenses suspension droplets from the jet nozzle by applying a force to the suspension in the nozzle as a droplet is needed to form the cell lawn or a colony of vectors.

When using ink jet methods to apply vector particles to gels, a particle suspension must be diluted to that the particles are applied separately, and each lytic spot contains only the progeny from one original vector particle. However, if the suspension is made too dilute, then lytic spots are widely separated and the clone selection process is inefficient. Therefore, a separate procedure using petri dishes may be used which has been calibrated against the film process described herein to prepare the dilution to be applied to the film.

When insert-containing cells such as yeast cells are employed, cell-sorter techniques may be used to identify droplets which contain single cells, and deposit these in a uniform pattern on the film surface. The cells are identified in the liquid stream by scatter of a laser beam by cells, and the droplets containing individual cells are electrostatically charged and directed to the next vacant spot. A fluorescent dye may be included in the stream to allow verification that individual droplets are reaching the film and are being evenly spaced.

Instead of the ink jetting methods of applying vectors to the gel, standard methods may be used in which a bottom agar composed of 1.5% agar-medium is applied to the film first, and then a cooling agar solution containing 0.75% agar with cells (typically *E. coli*) and diluted vector (phage) are added to form a top film. Using this method, the film is also wound on reels and incubated under conditions which allow the vectors to multiply and form lytic spots which are scanned and sampled received therefrom as described above.

In a preferred embodiment of the invention, 70 mm motion picture-type Estar® base film with Type II perforations (American National Standard, KS-1870, PH22.36-1969) with a pitch of 0.1870 inch is employed. The spacers 86 are 3-4 mm square, and the depth of the valleys 90 is about 1.5 mm. A cement used to attach the spacers 86 may be any of a large variety of cements, such as a drying cement, a room temperature vulcanizing silicone rubber, or a thermosetting plastic cement (which is preferred for this invention).

The film 22 is prepared in lengths which typically vary from 50 to 500 feet, and is wound on reels with perforated sides to allow free air flow and stored in a sterile environment. The film 22 is sterilized with ethylene oxide or by irradiation, and the containment system in which the film is prepared may be additionally sterilized by ultraviolet light.

| | |
|---|---|
| Gelatin | 4% |
| Agarose | 1% |
| NaCl | 1% |
| Bacto-tryptone | 1% |
| Bacto-yeast extract | 1% |

| | |
|---|---|
| Water | 92% | with a pH adjusted to 7.5 with sodium hydroxide.

While the invention has been disclosed by reference to the details of various embodiments of the invention, it is understood that this disclosure is intended in an illustrative rather than in a limiting sense, as it is contemplated that modifications will occur to those skilled in the art, within the spirit of the invention and the scope of the appended claims.

What is claimed is:

1. An apparatus for isolating a sample of cloned phage or viral vectors comprising
   (a) a film carrying a gelled culture medium between spacers extending parallel to longitudinal edges of the film,
   (b) a lawn of cells growing on said culture medium, said cells characterized as being susceptible to infection by phage or viral vectors, said sample on the lawn of cells,
   (c) recovery means for selectively removing said sample from the lawn of cells and transferring said removed sample to a site remote from the film, said recovery means being a hammer assembly comprising a hammer, a tip at one end of said hammer, and a plunger, said plunger being movable into engagement with said hammer so as to strike said tip to cause said tip to impact said cell lawn and remove the sample from the cell lawn, and
   (d) drive means to move said film past said recovery means.

2. The apparatus of claim 1 wherein the gelled culture medium has a thickness of about 0.25 mm to about 3.00 mm.

3. The apparatus of claim 2 wherein the gelled culture medium has a thickness of about 0.50 mm to about 1.00 mm.

4. The apparatus of claim 1 wherein said film is in a rolled form having a plurality of superposed film layers and said spacers are configured to facilitate air circulation between successive layers of the rolled film to support cell growth.

5. The apparatus of claim 1 wherein said film includes an array of sprocket apertures adjacent its longitudinal edges, said sprocket apertures being configured to mesh with said drive means to move the film past the recovery means.

6. The apparatus of claim 5 wherein said drive means is actuable to unwind said film from a first rolled form, move the film past said recovery means, and rewind the film into a second rolled form.

7. The apparatus of claim 1 further comprising hammer support means and means selectively operable for separating the hammer from the hammer support means at a location remote from the film.

8. The apparatus of claim 7 wherein the hammer support means comprises a movable belt to which the hammer is removably attached.

9. The apparatus of claim 8 further comprising a sample vessel positioned such that the hammer will be delivered therein at a location remote from the film.

10. The apparatus of claim 1 further comprising a scanning means for detecting the position of the sample on the cell lawn.

11. The apparatus of claim 10 further comprising means for transmitting sample location information from the scanning means to the recovery means.

12. The apparatus of claim 11 wherein said means for transmitting sample location information is a microprocessor.

13. The apparatus of claim 12 wherein said microprocessor is constructed so as to control the synchronized movement of the film, the hammer support means and the sample vessel.

14. The apparatus of claim 9 wherein said hammer comprises an elongate portion and a cap for the sample vessel.

15. The apparatus of claim 1 wherein said cells are E. coli.

16. An apparatus for isolating a sample of cloned cells comprising
   (a) a film carrying a gelled culture medium between spacers extending parallel to longitudinal edges of the film, said sample growing on the gelled culture medium;
   (b) recovery means for selectively removing said sample from the gelled culture medium and transferring the removed sample to a site remote from the film, said recovery means being a hammer assembly comprising a hammer, a tip at one end of said hammer, and a plunger, said plunger being movable into engagement with said hammer so as to strike said tip to cause said tip to impact said gelled culture medium and remove the sample from the gelled culture medium; and
   (c) drive means to move said film past said recovery means.

17. The apparatus of claim 16 wherein the gelled culture medium has a thickness of about 0.25 mm to about 3.00 mm.

18. The apparatus of claim 17 wherein the gelled culture medium has a thickness of about 0.50 mm to about 1.00 mm.

19. The apparatus of claim 16 wherein said film is in a rolled form having a plurality of superposed film layers and said spacers are configured to facilitate air circulation between successive layers of the rolled film to support cell growth.

20. The apparatus of claim 16 wherein said film includes an array of sprocket apertures adjacent its longitudinal edges, said sprocket apertures being configured to mesh with said drive means to move the film past the recovery means.

21. The apparatus of claim 20 wherein said drive means is actuable to unwind said film from a first rolled form, move the film past said recovery means, and rewind the film into a second rolled form.

22. The apparatus of claim 16 further comprising hammer support means and means selectively operable for separating the hammer from the hammer support means at a location remote from the film.

23. The apparatus of claim 22 wherein the hammer support means comprises a movable belt to which the hammer is removably attached.

24. The apparatus of claim 23 further comprising a sample vessel positioned such that the hammer will be delivered therein at a location remote from the film.

25. The apparatus of claim 24 wherein the hammer comprises an elongate portion and a cap for the sample vessel.

26. The apparatus of claim 25 further comprising a scanning means for detecting the position of the sample on the gelled culture medium.

27. The apparatus of claim 26 further comprising means for transmitting sample location information from the scanning means to the recovery means.

28. The apparatus of claim 27 wherein said means for transmitting sample location information is a microprocessor.

29. The apparatus of claim 28 wherein said microprocessor is constructed so as to control the synchronized movement of the film, the hammer support means and the sample vessel.

30. An apparatus for isolating a sample of cloned phage or viral vectors comprising
   (a) a film carrying a gelled culture medium between spacers extending parallel to longitudinal edges of the film,
   (b) a lawn of cells growing on said culture medium, said cells characterized as being susceptible to infection by phage or viral vectors, said sample growing on the lawn of cells,
   (c) recovery means for selectively removing said sample from the lawn of cells and transferring said removed sample to a site remote from the film, said recovery means being a filament of heat sterilizable material which contacts the sample to remove the sample form the cell lawn, and
   (d) drive means to move said film past said recovery means.

31. The apparatus of claim 30 wherein said filament is substantially V-shaped and is attached to a movable arm.

32. An apparatus for isolating a sample of cloned cells comprising
   (a) a film carrying a gelled culture medium between spacers extending parallel to longitudinal edges of the film, said sample growing on the gelled culture medium,
   (b) recovery means for selectively removing said sample from the gelled culture medium and transferring the removed sample to a site remote from the film, said recovery means being a filament of heat sterilizable material which contacts the sample to remove the sample form the cell lawn, and
   (c) drive means to move said film past said recovery means.

33. The apparatus of claim 32 wherein said filament is substantially V-shaped and is attached to a movable arm.

* * * * *